US010653787B2

(12) United States Patent
Levine et al.

(10) Patent No.: US 10,653,787 B2
(45) Date of Patent: May 19, 2020

(54) WATER-BASED CANNABINOID AND OPIOID COMPOSITIONS

(71) Applicant: IZUN PHARMACEUTICALS CORP., New York, NY (US)

(72) Inventors: William Z. Levine, Jerusalem (IL); Shmuel Cohen, Nehosha (IL)

(73) Assignee: IZUN PHARMACEUTICALS CORP, New York, NY (US)

( * ) Notice: Subject to any disclaimer, the term of this patent is extended or adjusted under 35 U.S.C. 154(b) by 0 days.

(21) Appl. No.: 14/661,573

(22) Filed: Mar. 18, 2015

(65) Prior Publication Data

US 2015/0265720 A1    Sep. 24, 2015

Related U.S. Application Data

(60) Provisional application No. 61/954,634, filed on Mar. 18, 2014, provisional application No. 62/096,558, filed on Dec. 24, 2014.

(51) Int. Cl.

| | | |
|---|---|---|
| *A61K 36/00* | (2006.01) | |
| *A61K 47/48* | (2006.01) | |
| *A61K 47/64* | (2017.01) | |
| *A61K 31/352* | (2006.01) | |
| *A61K 36/185* | (2006.01) | |

(52) U.S. Cl.
CPC ...... *A61K 47/48284* (2013.01); *A61K 31/352* (2013.01); *A61K 36/185* (2013.01); *A61K 47/643* (2017.08); *A61K 2236/00* (2013.01)

(58) Field of Classification Search
CPC .................................................. A61K 36/00
USPC ....................................................... 424/725
See application file for complete search history.

(56) References Cited

U.S. PATENT DOCUMENTS

| | | | | |
|---|---|---|---|---|
| 4,933,363 A | * | 6/1990 | Elsohly ................. | A61K 31/35 514/454 |
| 6,383,513 B1 | | 6/2002 | Watts | |
| 6,630,507 B1 | | 10/2003 | Hampson et al. | |
| 6,730,330 B2 | | 5/2004 | Whittle | |
| 7,622,140 B2 | | 11/2009 | Whittle | |
| 7,790,400 B2 | * | 9/2010 | Jehanli ................. | G01N 33/50 435/7.1 |
| 8,445,034 B1 | | 5/2013 | Coles | |
| 2012/0196873 A1 | | 8/2012 | Nolte | |

FOREIGN PATENT DOCUMENTS

| | | |
|---|---|---|
| GB | 2404023 | 1/2005 |
| KR | 20010052072 | 6/2001 |
| WO | WO 2010/124280 | * 10/2010 |
| WO | 2013165251 | 11/2013 |

OTHER PUBLICATIONS

Analysis of Cannabinoids in Hemp Seed Oils by HPLC using PDA detection, perrkin elmer, 2015.*
Chemistry and Analysis of Phytocannabinoids and other cannis constitutents, chapter 2, pp. 17-49, 2016.*
Mark J. Pletcher et al.; "Association Between Marijuana Exposure and Pulmonary Function Over 20 Years" Jan. 11, 2012, vol. 307, No. 2 pp. 173-181.
Timna Naftali et al.; "Treatment of Crohn's Disease with Cannabis: An Observational Study" Aug. 2011, IMAJ vol. 13, pp. 455-457.
Robert Melamede; "Cannabis and tobacco smoke are not equally carcinogenic" Harm Reduction Journal, Oct. 18, 2005, pp. 1-4.
Donald E. Greydanus et al "Fontiers in Public Health" Marijuana, current concepts, Oct. 10, 2013, pp. 1-17.
Rudolf Brenneisen; "Chemistry and Analysis of Phytocannabinoids and other Cannabis Constituents"; Chemistry of Cannabis Constituents; from Forensic Science and Medicine: Marijuana and the Cannabinoids, Chapter 2, pp. 17-49, 2007; Edited by M.S. ElShohly, Humana Press Inc., Totowa, New Jersey.
S. Casano; "Variations in Terpene Profiles of Different Strains of *Cannabis sativa* L." , pp. 115-122.
DeBacker et al.; Innovative development and validation of an HPLC/DAD method for the qualitive and quantitive determination of major cannabinoids in cannabis plant material; Journal of Chromatography B, 877 (2009), pp. 4115-4124.
European Search Report dated Nov. 24, 2017, for corresponding application No. 15764519.3 filed Oct. 14, 2016.
Grotenhermen F., Clinical Pharmacokinetics of Cannabinoids, Journal of Cannabis Therapeutics, vol. 3, No. 1, Jan. 31, 2003, pp. 3-51.
Haque S J, Poddar M, Interactions of cannabinoids with bovine serum albumin, Bioscience reports vol. 4, Mar. 31, 1984, pp. 239-243.
Kratz F. Albumin as a drug carrier: Design of prodrugs, drug conjugates and nanoparticles, Journal of Controlled Release, vol. 132, Jun. 30, 2008, pp. 171-183.
PCT Search Report dated Jun. 30, 2015 for PCT/IB2015/051991 filed Mar. 18, 2015.

* cited by examiner

*Primary Examiner* — Michael V Meller

(74) *Attorney, Agent, or Firm* — JMB Davis Ben-David

(57) ABSTRACT

Embodiments of the invention relate to methods for the manufacture of a protein-bound cannabinoid, comprising: obtaining a cannabinoid or cannabis in a form selected from the group consisting of cannabis smoke, cannabis vapor, cannabinoid solution and cannabis extract, and combining the cannabis smoke, vapor, cannabinoid solution or cannabis extract with an aqueous solution or suspension comprising a plasma protein to form a protein-bound cannabinoid. Further embodiments relate to aqueous solutions comprising a plasma protein-bound cannabinoid and pharmaceutical compositions comprising cannabinoids bound to plasma protein.

9 Claims, 6 Drawing Sheets

WATER-BASED CANNABINOID AND OPIOID COMPOSITIONS

RELATED APPLICATIONS

The present application claims the benefit under 35 U.S.C. 119(e) of U.S. Provisional Application 61/954,634 filed on Mar. 18, 2014 and U.S. Provisional Application 62/096,558 filed on Dec. 24, 2014, the disclosures of which are incorporated herein by reference.

TECHNICAL FIELD

Embodiments of the invention relate to compositions comprising cannabinoids.

BACKGROUND

*Cannabis* is a genus of plants comprising the species *Cannabis sativa, C. indica,* and *C. ruderalis*. Cannabis plants have been cultivated for a variety of uses including making fibers (hemp), medicinal use and recreational drug use. Cannabis is also commonly known as marijuana.

One of the most common ways that cannabis is used for medicinal use in many countries (also known as medical marijuana) is through smoking. Smoking cannabis is typically performed by using a pipe, by using a water-pipe (also known as a bong) which filters the smoke through water before inhalation or by rolling in paper to form marijuana cigarettes, also known colloquially as "joints." The part of the plant typically used for smoking is the whole flower and budding leaf.

Cannabinoids are compounds active on cannabinoid receptors in humans. Cannabinoids of plant origin, also known as phyto-cannabinoids, are abundant in plants of the *Cannabis* genus. Two known cannabinoids which are present in relatively high concentrations in *Cannabis sativa* are tetrahydracannabinol-acid (THCA) or its decarboxylated product tetrahydracannabinol (THC) and cannabidiolic acid (CBDA) or its decarboxylated product cannabidiol (CBD). Psychoactive and other medical effects of many of the cannabinoids have been studied. For example, THC was found to have psychoactive (calming) effects, analgesic effects, antioxidant effects and to increase appetite. CBD was found to have neuroprotective effects and to have ameliorative effects in patients with schizophrenia and Parkinson's disease. Additional cannabinoids, active cannabis compounds and their effects are disclosed in ElSohly et al., incorporated herein by reference.

In addition to cannabinoids, terpenoids and flavonoids are present in cannabis species. Some terpenoids were found to have biological effect and to contribute to a portion of the pharmacological effects of cannabis plant matter. Exemplary terpenoids present in cannabis plant matter include Beta-myrcene and alpha-pinene. Terpenoids and their identification is further described in Casano et al., incorporated herein by reference.

Although individual chemical components of cannabis have been isolated, many jurisdictions approve the use and sale of medical cannabis plant matter for a variety of indications. Research has shown that there are potential benefits to medical cannabis including but not limited to: pain relief, such as chronic pain or cancer related pain, neuropathic pain; lack of appetite, and nausea such as in patients with HIV/AIDS and in patients receiving chemotherapy; autoimmune disease, such as multiple sclerosis; epilepsy; glaucoma; neurodegenerative disease and post-traumatic stress disorder (PTSD). (Greydanus, 2013) Inflammatory disease, such as Crohn's disease is another indication in which cannabis may have a positive effect. (Naftali, 2011)

Smoking medical cannabis, although proven to be beneficial in certain indications, has disadvantages. Since cannabis is a plant, amounts of active ingredients in the part of the plant being smoked may differ depending on the part of the plant and from plant to plant. Changing growing conditions (such as amount of light that a plant receives per day, or temperature) may vary at a cannabis growing facility thereby providing product in which concentration of active ingredients vary over the course of the year. As a result, a patient treated using medical cannabis may lack control over proper dosing of active cannabinoids.

Another disadvantage of smoking medical cannabis is the negative impact of some of the constituents of cannabis smoke. The smoke from the plant matter may comprise carcinogens in addition to the desired cannabinoids. (Melamede, 2005) In addition, heavy cannabis use through smoking has been associated with accelerated pulmonary decline. (Pletcher, 2012)

Opium is a naturally occurring latex which is obtained from resin of the flower bud of the opium poppy plant known as *Papaver sombiferum*. Opium and other plant matter from the opium poppy comprise many pharmaceutically active compounds known as opioids, including, for example, morphine and codeine. Opium is a drug used in ancient as well as modern times, as morphine is effective in a variety of indications and is effective in providing analgesia, treating various types of pain and alleviating shortness of breath in patients. Opium may be administered via smoking or vaporization by heating the opium and by subsequent inhalation of the smoke or vapor.

Opium administration by smoking and/or vaporization of opium poppy plant matter, may be disadvantageous in side effects of smoking as well as lack of control over dosing, as addressed with respect to cannabis.

SUMMARY

Embodiments of the invention provide compositions comprising cannabinoid components of cannabis plant or of smoke derived from cannabis plant. Such compositions may mimic interactions between plasma proteins and smoke/vapor comprising cannabinoids. Such compositions may obviate the need for a patient to smoke cannabis and thereby experience the detrimental effects associated with cannabis smoke inhalation. Methods for making such compositions are also provided herein. The novel compositions may be water soluble, allowing for preparation of quality controlled, accurately dosed pharmaceutical compositions for administration and rapid absorption by humans. The compositions may be characterized and quantified so that a patient can receive a measured quantity of an active cannabinoid or a combination of a plurality of cannabinoids, or other active compounds in the cannabis plant. The compositions may provide pharmacological benefits similar to those associated with cannabis smoke, but without the detrimental effects associated with cannabis smoke inhalation.

An aspect of an embodiment of the invention provides a method for the manufacture of a protein-bound cannabinoid, the method comprising: heating cannabis plant matter to form a smoke and/or a vapor, and introducing the smoke and/or vapor to an aqueous solution or suspension comprising a protein. Further embodiments relate to methods for isolation of an active cannabinoid from cannabis comprising: heating cannabis plant matter to form a smoke and/or a vapor, and introducing the smoke and/or vapor to an aqueous solution comprising a protein.

Further embodiments of the invention relate to novel compositions derived from cannabis extract or heated cannabis extract or cannabis smoke/vapor dissolved in solvent. Cannabis extract may comprise multiple cannabinoids derived from the plant matter from which it is derived. The cannabis extract may be combined with aqueous protein to bind cannabinoids present in the extract to aqueous proteins.

Compositions, according to embodiments of the invention may comprise a cannabinoid or at least two cannabinoids bound to protein in an aqueous medium, and optionally a pharmaceutically acceptable carrier.

Cannabinoids generally have very low solubility in water. This quality has previously caused difficulty in forming aqueous pharmaceutical compositions or extracts based on cannabis. It has been found that because of low solubility of cannabinoids in water, introducing cannabis extract or smoke/vapor into an aqueous medium alone, does not significantly allow for the dissolution of cannabinoids in the aqueous medium. On the other hand, when a plasma protein such as albumin is introduced into the aqueous medium before the introduction of the cannabis extract or smoke/vapor, active cannabinoids are bound by the protein and can dissolve in the aqueous solution.

According to an embodiment of the invention, aqueous solution comprising cannabinoids bound to proteins may be purified and/or quantified to determine the identity and quantity of individual cannabinoids in it. Separation of cannabinoids from each other may then also be performed.

Plasma proteins have regions with an affinity to hydrophobic molecules such as drugs, hormones or hydrophobic amino acids. Without being bound by theory, it is suggested that when cannabis smoke/vapor is introduced to an aqueous solution comprising a plasma protein, the plasma protein may bind to the cannabinoids in the smoke/vapor. It is further suggested that when cannabis extract is introduced to an aqueous solution comprising a plasma protein, the plasma protein may bind to the cannabinoids in the extract. The aqueous solution that results may then be purified to remove non-bound chemical components that originated in the cannabis extract or smoke/vapor and that had dissolved in the aqueous solution. The cannabinoids that are bound by proteins, and in particular plasma proteins such as albumin, lipoprotein, glycoprotein, and $\alpha$, $\beta$, and $\gamma$ globulins, may be introduced into the body of a patient in need thereof. The plasma protein-bound cannabinoid may then circulate within the plasma and interact with specialized plasma proteins receptors or release the cannabinoid within the body, providing a desired pharmacological effect. The plasma protein-bound cannabinoid may have a different pharmacological effect substantially equivalent to or greater than the cannabis smoke/vapor from which it originated, without the deleterious effects associated with inhalation of cannabis smoke.

According to an embodiment of the invention, a plasma protein may incorporate a complete plasma protein or a peptide comprising a portion of a plasma protein. The portion of the plasma protein may comprise a portion which adsorbs a cannabinoid. According to an embodiment of the invention, a plasma protein is a variant of a naturally occurring plasma protein.

An embodiment of the invention relates to a targeting plasma protein-bound cannabinoid which comprises a targeting moiety linked to the plasma protein. The targeting moiety may be a molecule that binds to a ligand having prevalence in a certain organ or cell type in a patient. For example, the ligand may be a ligand prevalent in a cancer and less prevalent in non-cancer cells. An advantage of such an embodiment is the ability to target a plasma protein-bound cannabinoid to a specific organ or type of cell or to prevent the cannabinoids from entering the central nervous system.

Without being bound by theory, it is suggested that when a patient smokes cannabis plant matter, the cannabinoids in the smoke/vapor which is introduced into his/her lungs are absorbed into the patient's blood stream and carried or bound by plasma proteins. Compositions according to embodiments of the invention may be beneficial in that active cannabinoids are bound by plasma proteins and easily absorbed in the bloodstream of the patient.

An aspect of an embodiment of the invention provides a method for the manufacture of a protein-bound opioid, the method comprising: heating opium plant matter to form a smoke and/or a vapor, and introducing the smoke and/or vapor to an aqueous solution or suspension comprising a protein. Such methods yield novel compositions with enhanced qualities such as enhanced bioavailability.

Further embodiments of the invention relate to novel compositions derived from cannabis, comprising terpenoids and/or flavonoids.

Further embodiments of the invention relate to novel compositions derived from opium plant matter. Opium plant matter may comprise various opioids. The plant matter, or extract made from the plant matter may be combined with aqueous protein to bind opioids to aqueous proteins.

Compositions, according to embodiments of the invention may comprise an opioid or at least two different opioids, bound to protein in an aqueous medium, and optionally a pharmaceutically acceptable carrier.

Naturally occurring opioids may have low solubility in water. This quality has previously caused difficulty in forming aqueous pharmaceutical compositions or extracts based on opium. It is suggested that because of low solubility of opium in water, introducing opium smoke/vapor into an aqueous medium alone, does not significantly allow for the dissolution of opioids in the aqueous medium. On the other hand, when a plasma protein such as albumin is introduced into the aqueous medium before the introduction of the opium extract or opium smoke/vapor, active opioids may be bound by the protein and may dissolve in the aqueous solution.

Naturally occurring pharmaceutically active ingredients from other plants or animals may be bound to proteins using methods described herein using similar methods to those presented herein with respect to cannabis. Non-limiting examples of such naturally occurring pharmaceutically active ingredients include: steroids, such as ecdysteroids and phytoecdysteroids.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear.

DETAILED DESCRIPTION

Figure 1A:
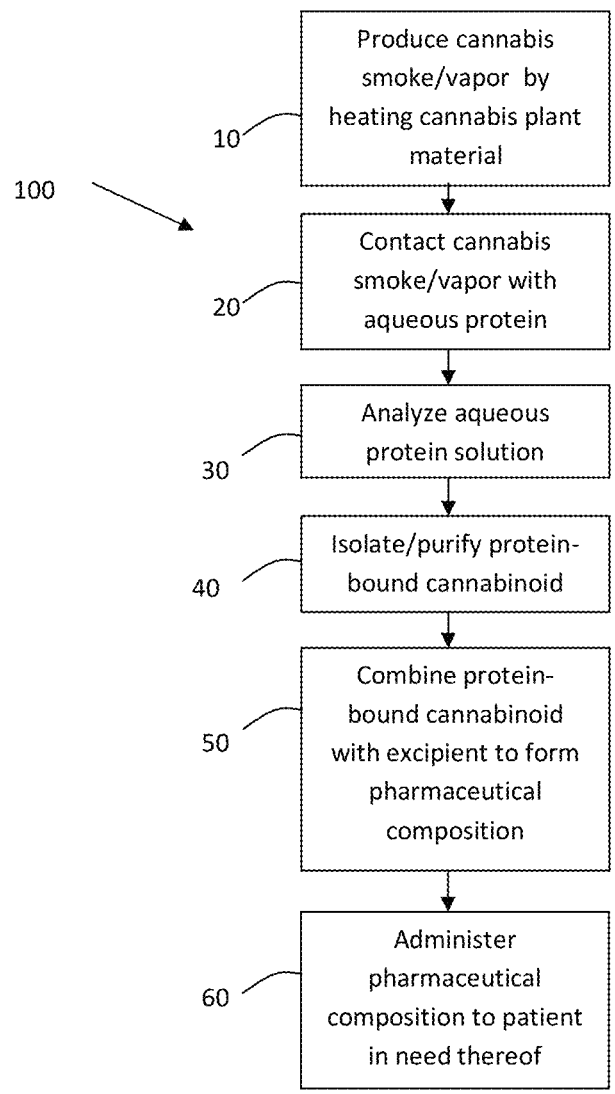
FIGS. 1A and 1B show flow diagrams depicting processes according to embodiments of the invention.

In the following detailed description, new methods for manufacture of enhanced compositions comprising cannabinoids will be described in detail. Reference is now made to FIG. 1A, which shows a flow-diagram depicting a method 100 for the manufacture of compositions comprising cannabinoids and/or for treatment of a patient in need thereof, in accordance with embodiments of the invention.

Method 100 comprises a block 10, which comprises producing cannabis smoke and/or vapor by heating cannabis plant material. According to an embodiment of the invention, cannabis plant material may be selected from one or more than one of: leaves, flowers, trichomes, resin, tincture, extract, oil and cannabis tissue culture parts like callus. According to an embodiment, cannabis plant material comprises a combination of leaves and flowers.

According to an embodiment of the invention, cannabis plant material may comprise a material from a cannabis species selected from the group consisting of: *Cannabis sativa, C. indica*, and *C. ruderalis*. In an embodiment, the cannabis species is a mixed species based on at least one of the aforementioned cannabis species. In a preferred embodiment, the cannabis plant material comprises *C. sativa*.

According to an embodiment of the invention, smoke is produced by combustion or burning of cannabis plant material. In an embodiment, smoke/vapor is produced by heating the plant material to a temperature of between about 40° C. and to about the combustion temperature of the plant material. Combustion and/or heating of the cannabis plant matter may be performed in a chamber suitable for collection of vapor and/or smoke formed upon the combustion and/or heating.

Method 100 may further comprise a block 20, which comprises contacting cannabis smoke/vapor with an aqueous protein solution.

According to an embodiment of the invention, the protein is a plasma protein. According to an embodiment of the invention, the plasma protein is one of or a combination of more than one of albumin, lipoprotein, glycoprotein, and α, β, and γ globulin or diluted blood plasma. According to an embodiment of the invention, the plasma protein may be naturally occurring protein or recombinant protein. According to an embodiment of the invention, the albumin may comprise human serum albumin or bovine serum albumin or egg albumin (OVA).

Contacting the cannabis smoke/vapor with an aqueous protein solution may be performed by collecting the smoke/vapor and bubbling it through the aqueous protein solution. Optionally, a forced-air vaporizer may be used to contact cannabis smoke/vapor with an aqueous protein solution. Optionally, a system may be used in which smoke/vapor is streamed in to the albumin solution stream using the Venturi effect having pipes for conducting the fluids, the pipes having varying diameters.

According to an embodiment of the invention, the aqueous solution comprises at least one salt and at least one buffer. According to an embodiment of the invention, the solution is substantially isotonic with blood. According to an embodiment, the solution comprises Hartmann's solution.

According to an embodiment of the invention the aqueous solution comprises between about 0.001% and about 80% plasma protein on a weight/volume (w/v) basis. According to an embodiment of the invention the aqueous solution comprises between about 0.01% and about 40% plasma protein on a w/v basis According to an embodiment, the aqueous solution comprises about 20% (w/v) plasma protein. According to an embodiment of the invention, the concentration of protein is about 10 mg/ml.

According to an embodiment of the invention, the aqueous solution may comprise an additional non-water solvent. According to an embodiment of the invention, the non-water solvent is an alcohol. According to an embodiment of the invention, the alcohol may comprise ethanol. According to an embodiment of the invention, the aqueous solution may comprise a non-water solvent in a concentration of about 25%-33%.

Upon contacting a cannabis smoke with an aqueous protein solution, the protein in the aqueous solution may bind cannabinoids present in the smoke, forming protein-bound cannabinoid. The otherwise water-insoluble cannabinoid may then be dissolved in the aqueous protein solution.

Method 100 may further comprise a block 30, which comprises analyzing the aqueous protein solution. Analysis may be performed on a sample of the aqueous solution or the purified wash protein to determine the cannabinoid profile (identity and quantity) of the cannabis plant material. Analysis may be performed through chromatography, such as gas chromatography or HPLC.

Method 100 may further comprise a block 40, which comprises isolating and/or purifying protein-bound cannabinoid. According to an embodiment of the invention, isolating and or purifying protein-bound cannabinoid may comprise removing non-protein-bound dissolved compounds from the solution. This may be performed by precipitating the protein-bound cannabinoid out of solution, for example, by adding a solvent or a salt to the solution or by denaturing the protein, for example, by heating. The precipitate may then be washed to remove non-protein bound dissolved components. According to an embodiment of the invention, purification may be performed through a pore-size gradient or using a dialysis tube.

Alternatively or additionally, purification of protein-bound cannabinoid may be performed by removal of water from the solution, according to embodiments of the invention. Removal of the water may be performed by vacuum, heating, lyophilization, or a combination of any of these methods.

Method 100 may further comprise a block 50, which comprises combining a protein-bound cannabinoid with an excipient to form a pharmaceutical composition.

The protein-bound cannabinoid according to an embodiment of the invention may comprise one or more than one of the following: Δ9-THC, Δ8-THC, tetrahydrocannabinoic acid (THCA), CBD, cannabidiolic acid (CBDA), cannabinol (CBN), cannabigerol (CBG), tetrahydrocannabivarin (THCV), cannabigerolic acid CBGA and cannabichromene (CBC).

The pharmaceutical compositions according to an embodiment of the invention are conveniently presented in unit dosage form and are prepared by any of the methods well known in the art of pharmacy. In an embodiment of the invention, the unit dosage form is in the form of a tablet, capsule, lozenge, wafer, patch, ampoule, vial, metered-dose inhaler or pre-filled syringe.

The compositions of the present invention are generally administered in the form of a pharmaceutical composition comprising at least one active component together with a pharmaceutically acceptable carrier or diluent.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tableting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the components of this invention can be combined with various sweetening agents, flavoring agents, coloring agents, emulsifying agents and/or suspending agents, as well as such diluents as water, ethanol, propylene glycol, glycerin and various like combinations thereof.

The compositions according to embodiments of this invention may also be administered in a controlled release formulation such as a slow release or a fast release formulation. Such controlled release dosage composition may be prepared using methods well known to those skilled in the art.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

Pharmaceutical compositions according to embodiments of the invention may contain an active amount of 0.1%-95% of the protein-bound cannabinoid(s) (based on total cannabinoid weight) preferably 1%-70%.

In an embodiment of the invention, the daily dosage of the protein-bound cannabinoid, is between 0.1 microgram (μg) and 1500 milligram (mg). Some embodiments of the invention relate to treatments as monotherapy, in which a protein-bound cannabinoid is a sole active pharmaceutical agent used to treat a disease. Some embodiments of the invention relate to combination therapies in which a protein-bound cannabinoid is used in combination with another active pharmaceutical agent to treat a disease. "In combination with" refers to both drugs being substantially effective in the body at a same time. Both drugs can be administered substantially at the same time, or both drugs can be administered at different times but have effect on the body at the same time.

Method 100 may further comprise a block 60, which comprises administering the pharmaceutical composition to a patient in need thereof.

The above mentioned method 100 may be practiced with respect to opium poppy plant matter in order to obtain opioids, by replacing cannabis plant matter with opium poppy plant matter.

Figure 1B:
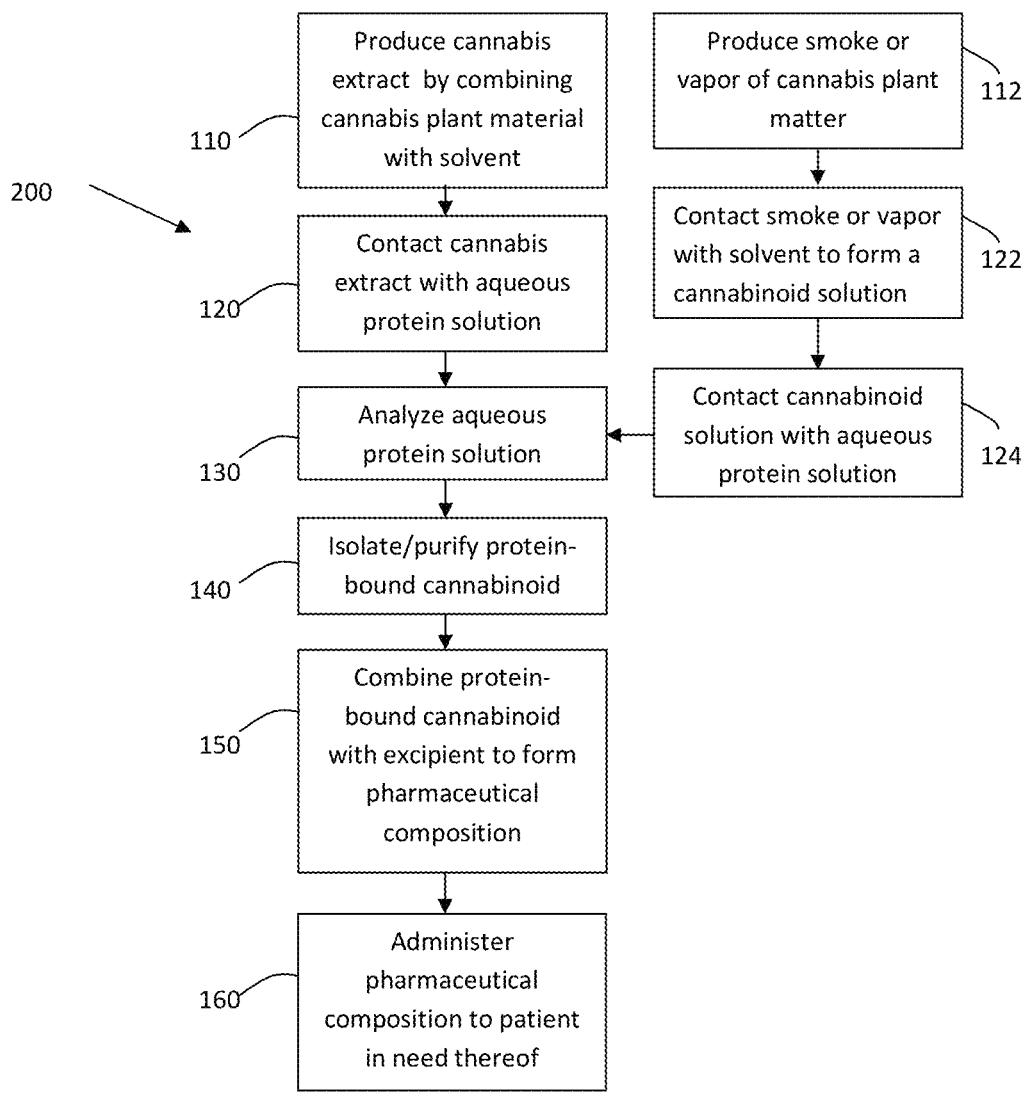

Reference is now made to FIG. 1B, which shows a flow-diagram depicting a method 200 for the manufacture of compositions comprising cannabinoids and/or for treatment of a patient in need thereof, in accordance with embodiments of the invention.

Method 200 comprises a block 110, which comprises producing cannabis extract from cannabis plant material. According to an embodiment of the invention, cannabis plant material may be selected from one or more than one of: leaves, flowers, trichomes, resin, tincture, extract and oil. According to an embodiment, cannabis plant material comprises a combination of leaves and flowers. According to an embodiment of the invention, cannabis extract is prepared by contacting cannabis plant material with a solvent. According to an embodiment the solvent comprises an alcohol. According to an embodiment of the invention, the alcohol comprises methanol or ethanol. According to an embodiment of the invention, the solvent is a mixture of methanol and chloroform.

Method 200 may further comprise a block 120, which comprises contacting cannabis extract with an aqueous protein solution.

According to an embodiment of the invention, the protein is a plasma protein. According to an embodiment of the invention, the plasma protein is one of or a combination of more than one of albumin, lipoprotein, glycoprotein, and α, β, and γ globulin or diluted blood plasma or egg albumin (OVA). According to an embodiment of the invention, the plasma protein may be naturally occurring protein or recombinant protein. According to an embodiment of the invention, the albumin may comprise human serum albumin or bovine serum albumin or egg albumin or any combination thereof.

Contacting the cannabis extract with an aqueous protein solution may be performed using 0.1% to 33% cannabinoids extract (in solvent) in an aqueous solution. According to an embodiment of the invention, the aqueous solution is mixed slowly and/or incubated from a time between 10 minutes and 48 hours.

According to an embodiment of the invention, the aqueous solution comprises at least one salt and at least one buffer. According to an embodiment of the invention, the solution is substantially isotonic with blood. According to an embodiment, the solution comprises Hartmann's solution. Alternatively, the solution may be water.

According to an embodiment of the invention the aqueous solution comprises between about 0.001% and about 80% plasma protein on a weight/volume (w/v) basis. According to an embodiment of the invention the aqueous solution comprises between about 0.01% and about 40% plasma protein on a w/v basis. According to an embodiment, the aqueous solution comprises about 20% (w/v) plasma protein.

Upon contacting a cannabis extract with an aqueous protein solution, the protein in the aqueous solution may bind cannabinoids present in the extract, forming protein-bound cannabinoid. The otherwise water-insoluble cannabinoid may then be dissolved in the aqueous protein solution.

Method 200 may further comprise a block 112, comprising smoke or vapor of cannabis plant matter. Smoke or vapor may be formed as in method 100, block 10.

Method 200 may further comprise a block 122, comprising contacting smoke or vapor with a solvent to form a cannabinoid solution. The solvent, according to an embodiment of the invention, may be an alcohol. The alcohol may be ethanol.

Method 200 may further comprise a block 124, comprising contacting cannabinoid solution with an aqueous protein solution. Contacting of block 124 may be similar to the contacting of cannabis extract of block 120, with the modification of substituting a cannabinoid solution for a cannabis extract.

Method 200 may further comprise a block 130, which comprises analyzing the aqueous protein solution. Analysis may be performed on a sample of the aqueous solution to determine the cannabinoid profile (identity and quantity) of the cannabis plant material. Analysis may be performed through chromatography, such as gas chromatography or HPLC.

Method 200 may further comprise a block 140, which comprises isolating and/or purifying protein-bound cannabinoid. According to an embodiment of the invention, isolating and or purifying protein-bound cannabinoid may comprise removing non-protein-bound dissolved compounds from the solution. This may be performed by precipitating the protein-bound cannabinoid out of solution, for example, by adding a solvent or a salt to the solution or by denaturing the protein, for example, by heating. The precipitate may then be washed to remove non-protein bound dissolved components. According to an embodiment of the invention, purification may be performed through a pore-size gradient.

Alternatively or additionally, purification of protein-bound cannabinoid may be performed by removal of water from the solution, according to embodiments of the invention. Removal of the water may be performed by vacuum, heating, lyophilization, or a combination of any of these methods.

Method 200 may further comprise a block 150, which comprises combining a protein-bound cannabinoid with an excipient to form a pharmaceutical composition.

The protein-bound cannabinoid according to an embodiment of the invention may comprise one or more than one of the following: Δ9-THC, Δ8-THC, tetrahydrocannabinoic acid (THCA), CBD, cannabidiolic acid (CBDA), cannabinol (CBN), cannabigerol (CBG), tetrahydrocannabivarin (THCV), cannabigerolic acid CBGA and cannabichromene (CBC).

According to an embodiment of the invention, the cannabinoids present in the protein-bound cannabinoid may be similar in profile as in the starting cannabis extract produced in block 110.

Method 200 may further comprise a block 160, which comprises administering the pharmaceutical composition to a patient in need thereof.

The above mentioned method 200 may be practiced with respect to opium poppy plant matter in order to obtain opioids, by replacing cannabis plant matter with opium poppy plant matter. According to an embodiment of the invention, administration is performed through inhalation. Inhalation may comprise inhalation via the nasal route or via the mouth. According to an embodiment of the invention, administration is performed through sublingual or buccal administration, oral administration, transdermal administration or parenteral administration.

According to an embodiment of the invention, the pharmaceutical composition is administered to the patient to treat a disease or condition. According to an embodiment of the invention, the disease or condition is selected from the group consisting of: conditions of pain relating to chemotherapy; conditions of pain and "wasting" syndrome in connection with AIDS; nausea and vomiting, nausea and vomiting as side effects of a chemotherapy as well as in connection with AIDS or hepatitis; neuropathic pain; anorexia or cachexia; neurodegenerative disease; hypoxia, comprising stroke or trauma; paralytic symptoms in connection with multiple sclerosis or traumatic transverse lesions; dystonic motor disturbance; bronchial asthma; epileptic attacks or generalized epilepsy; withdrawal symptoms in connection with alcohol dependence, benzodiazepine dependence and opiate dependence; Parkinson's disease; dementia, Alzheimer's disease; arthritis; glaucoma; migraine; PTSD; Crohn's disease; tremor, Parkinsonian tremor; attention deficit disorder; attention deficit hyperactivity disorder; irritable bowel syndrome and dysmenorrhoea.

Example 1a: Formation of Protein-Bound Cannabinoid from Cannabis Smoke

Protein-bound cannabinoid was formed according to the following method. An aqueous albumin solution was prepared by adding 20 (mg)) of bovine serum albumin (BSA, from Millipore, USA) to 10 milliliters (ml) ml Hartmann's solution (B. Braun Melsungen AG, Germany). BSA was completely dissolved using a shaker (Heidolph POLYMAX 1040) at 50 revolutions per minute.

A cannabis-filled cigarette was formed using a cigarette paper containing 0.8 gr ground cannabis (provided by "Seach" Israel), from flowers and budding leaves. A Pasteur pipette was cut longitudinally at its wide end, and the cigarette was lodged in to the cut end. The narrow end of the pipette was attached to a syringe. The cigarette was lit in a fume hood, and cigarette smoke was collected in the syringe by pulling the syringe plunger. The smoke was then slowly released into the BSA solution by depressing the plunger. Approximately 350 ml of smoke-containing air was gently bubbled through the BSA solution.

As a control, a solution of 10 ml of Hartmann's solution was prepared without the addition of BSA and a similar procedure of cannabis smoke formation and bubbling was performed.

Samples having a volume of 3 ml of the BSA solution and the control solution were each inserted in to HPLC glass vials and the open vials were inserted into a vacuum oven for 24 hours at 37° Celsius.

The solid phase after the evaporation was crushed in to a fine powder using mortar and pestle. The powder was extracted using Methanol chloroform 9:1 extract solution, sonicated for 30 minutes, and was then filtered and added in to an HPLC testing tube.

HPLC was performed using an HP1050 AGILENT, DAD detector, XBridge C18 3.5 μm 4.6×150 mm column, and according to the following parameters:

| | |
|---|---|
| Mobile Phase A | 50 mM ammonium formate in water at pH 3.75 with 10% ACN |
| Mobile Phase B | Mobile phase B: 90% ACN/10% Water |
| Diluent | water/acetonitrile (v/v: 5/5) |
| Flow Rate | 1 ml/min |
| Injection | 30 μl |
| Draw Speed | 200 μl/min |
| Eject Speed | 200 μl/min |
| Stop time | 40 min |
| Column Temperature | 30° C. |
| Detector | Diode array detector |
| Signal store | 228 nanometers (nm, non-acidic cannabinoids) 270 nm (acidic cannabinoids), Store spectrum from 190-370 nm |

Gradient Program:

| Time (min) | % A | % B |
|---|---|---|
| 0 | 30 | 70 |
| 15 | 10 | 90 |
| 30 | 10 | 90 |
| 31 | 30 | 70 |
| 40 | 30 | 70 |

Figure 2A:
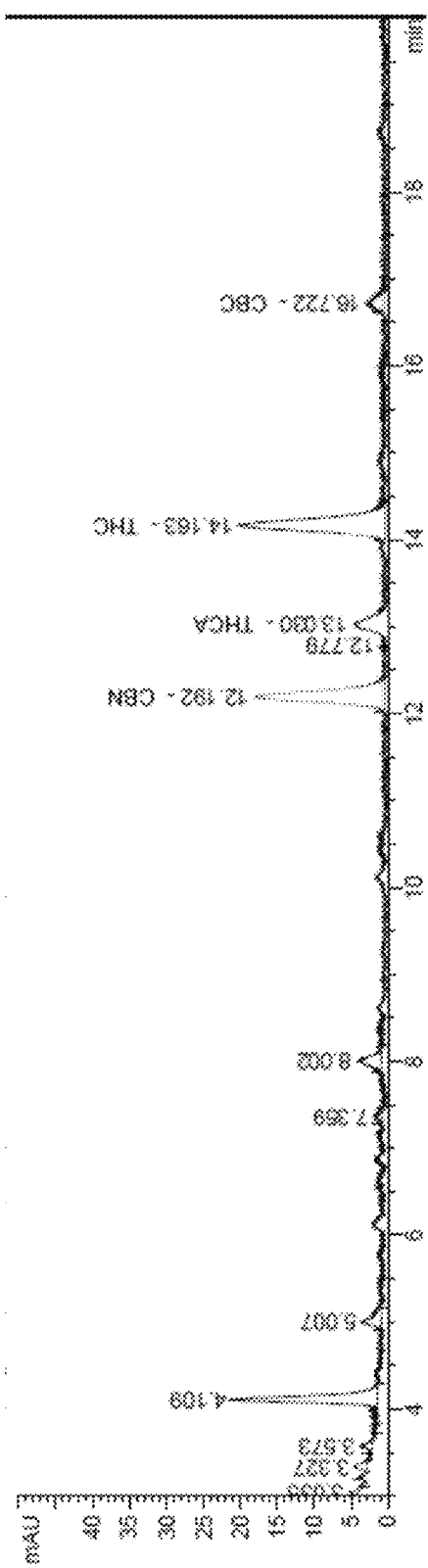
FIG. 2A depicts a chromatogram from a high performance liquid chromatography (HPLC) testing of a sample of protein-bound cannabinoids synthesized by exposing cannabis smoke to a plasma protein solution according to an embodiment of the invention.
Figure 2B:
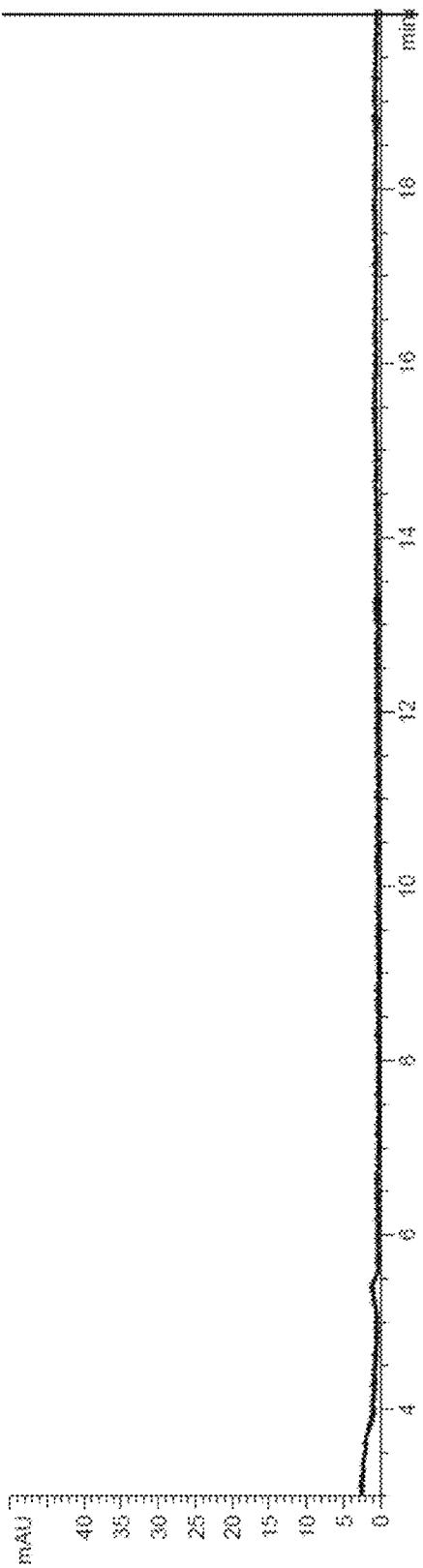
FIG. 2B depicts a chromatogram from an HPLC testing of a sample of control solution without proteins which was exposed to cannabis smoke.

Results:

HPLC showed that the BSA aqueous solution, after cannabis smoke was introduced to it, comprised many active cannabinoids including CBN, THCA, THC and CBC, which had dissolved in the solution. A corresponding chromatogram is shown in FIG. 2A, based on the 270 nm wavelength. The chromatogram shows peak intensity (in units of milli-absorbance units, mAU) over time in minutes. On the other hand, in the control solution which did not comprise proteins, no active cannabinoids were detected, as shown in FIG. 2B.

The inventors have shown that methods according to embodiments of the invention may effectively dissolve significant amounts of active cannabinoids from cannabis smoke/vapor in aqueous solutions using plasma proteins as agents to bind and enhance solubility of the cannabinoids. Aqueous solutions formed according to embodiments of the invention are advantageous in that they can be easily quantified, purified and formulated into pharmaceutical compositions for administration in a variety of routes. The cannabanoids profile of the aqueous solution is similar to that of the cannabis smoke/vapor, which has already been shown to be effective in treatment of a variety of diseases when administered via the lungs. At the same time, plasma protein-bound cannabinoids can be administered with more accuracy and without the negative lung health ramifications associated with smoking cannabis.

Example 1b: Formation of Protein-Bound Cannabinoids and Quantification of Cannabinoids In order to increase amount of protein-bound cannabinoid present in BSA/water solution according to example 1a, additional experimentation was performed using varying amounts of additional solvents. The range of between 25% and 33% ethanol was found to be particularly advantageous, particularly at 10 mg protein per ml of solution.

A solution was formed by forming a water solution having a concentration of 10 mg/ml of BSA. 50 ml of the water solution was mixed with 25 ml of ethanol. A 1 g cigarette of cannabis (provided by Seach, Israel, Batch B12) was lit and smoke was bubbled through the BSA/water/ethanol solution using the apparatus described in example 1a, but using a vacuum pump to gradually introduce the smoke into the solution via a gas trap. The solution foamed to a lesser extent than the solution used in example 1a.

After introducing smoke into the solution, the solution was split into three batches for incubation. Batch A was incubated for 1 hour at room temperature while stirring. Batch B was incubated at room temperature for 48 hours without stirring. Batch C was incubated at room temperature for 48 hours while stirring. Cannabinoid identity and quantity were determined by HPLC. The amount and type of cannabinoid varied based on the incubation conditions, as follows:

| Batch | Total Cannabinoid Content per mg BSA |
|---|---|
| A | 0.45 micrograms (μg) |
| B | 1.96 μg |
| C | 2.15 μg |

It was found that aqueous protein solutions comprising 33% ethanol had an approximately three-fold higher cannabinoid content per mg BSA than corresponding aqueous protein solutions having no non-water solvent.

Figure 5:
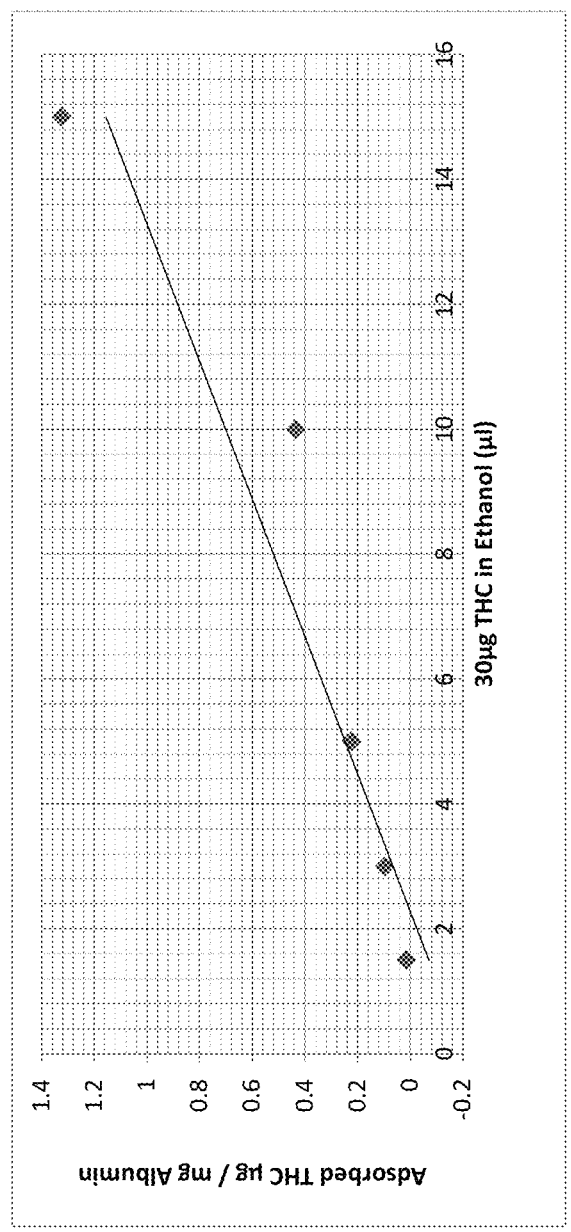
FIG. 5 depicts a graph shown effect of varying concentration of ethanol in aqueous solution and impact on THC adsorption to protein in resulting solutions.

Example 1c: Formation of Protein-Bound Cannabinoids in Solutions Comprising Various Concentration of Protein/Solvent 30 micrograms of THC standard was dissolved in various amounts of ethanol (absolute) in various amounts, between 1.5 microliters and 15 microliters. The THC solution was then combined with 0.5 ml of a 20 microgram/ml solution of BSA. The resulting solutions each had a total of 10 micrograms of BSA and 30 micrograms of THC, but varied in their ethanol content. As ethanol concentration increases, the adsorption of THC to protein increases. The results can be seen in FIG. 5.

The inventors found that solutions having a concentration of over 33% ethanol, it was seen that protein precipitates and a cloudy mixture was formed.

Example 1d: Formation of Protein-Bound Cannabinoids from Smoke and Vapor and Quantification Relative to Smoke or Vapor Absorbed in Organic Solvents To show which cannabinoid compounds are solubilized in processes using BSA versus organic solvents, cannabis from two different batches was smoked and or vaporized. Vapor was formed using a "volcano" vaporizer at a temperature of 210° C. The smoke/vapor was passed through either a BSA/water/ethanol solution described in example 1b, comprising 33% by volume ethanol or through a pure ethanol (99% ethanol) solution. Solutions were stirred using a magnetic stirrer and were incubated for 48 hours, during which time, most of the ethanol evaporated. One of the batches of cannabis was high in THC, and the other batch of cannabis was high in both THC and CBD.

The BSA/water/ethanol solution was washed after smoke or vapor was combined with it, and the amount of cannabinoids present was analyzed. The results of the comparison of relative concentration of cannabinoids (relative to total cannabinoid content) as expressed in percent (weight/weight), for a strain of cannabis high in THC are shown in the table below.

| Cannabinoid | Smoke passed through ethanol | Vapor passed through ethanol | Smoke passed through BSA/water/ethanol |
|---|---|---|---|
| CBDA (Cannabidiolic Acid) | 0.9 | 0.4 | 0.0 |
| CBGA (Cannabigerolic acid) | 0.6 | 0.1 | 0.0 |
| CBG | 4.9 | 1.2 | 21.0 |
| CBD | 1.9 | 0.3 | 0.0 |
| THCV | 2.4 | 0.7 | 0.0 |
| CBN | 1.7 | 1.6 | 0.0 |
| THCA | 0.9 | 1.1 | 9.3 |
| THC | 86.7 | 94.6 | 69.7 |
| DELTA-8-THC | 0.0 | 0.0 | 0.0 |
| CBC | 1.3 | 0.0 | 0.0 |

The results of the comparison of relative concentration of cannabinoids (relative to total cannabinoid content) as expressed in percent (weight/weight), for a strain of cannabis high in CBD and THC are shown in the table below.

| Cannabinoid | Smoke passed through ethanol | Vapor passed through ethanol | Smoke passed through BSA/water/ethanol | Vapor passed through BSA/water/ethanol |
|---|---|---|---|---|
| CBDA | 2.3 | 1.6 | 39.8 | 23.6 |
| CBGA | 0.4 | 0.0 | 0.0 | 0.0 |
| CBG | 4.2 | 1.5 | 0.0 | 0.0 |
| CBD | 44.7 | 51.1 | 22.3 | 33.4 |
| THCV | 2.4 | 0.8 | 0.0 | 0.0 |
| CBN | 1.6 | 0.0 | 0.0 | 0.0 |
| THCA | 0.7 | 0.3 | 5.3 | 0.0 |
| THC | 40.7 | 40.9 | 32.8 | 37.7 |
| DELTA-8-THC | 0.0 | 0.0 | 0.0 | 0.0 |
| CBC | 3.1 | 3.8 | 0.0 | 5..3 |

As can be seen from the tables above, a different cannabinoid profile is present when smoke or vapor is contacted with BSA water solution relative to ethanolic solvent. It is suggested that the profile of cannabinoid obtained when contacting with BSA water solution is similar to the profile absorbed in a human bloodstream after inhalation of cannabis smoke or vapor.

Example 1e: Determination of Adsorption Capacity of BSA Using THC Standard

Figure 4:
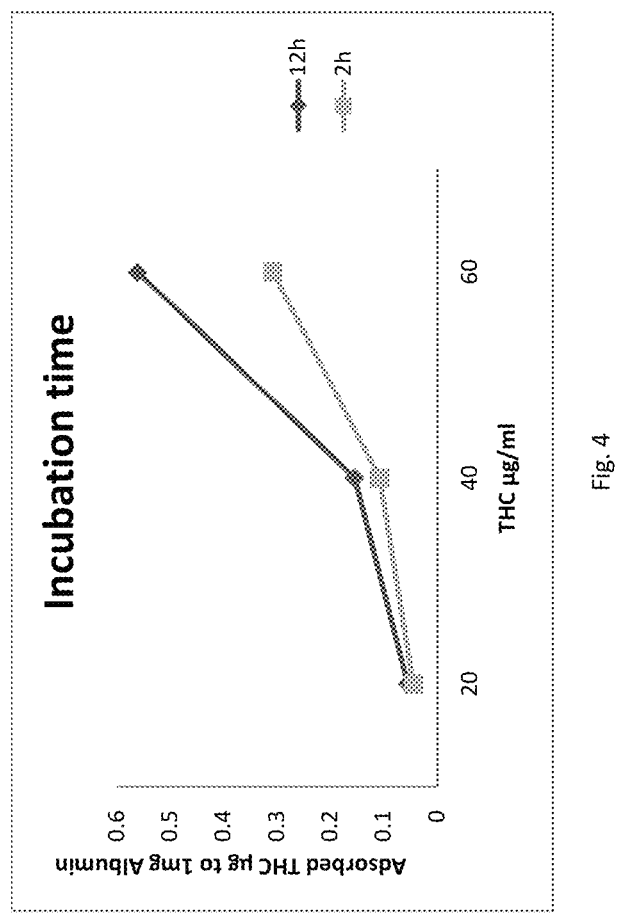
FIG. 4 depicts a graph showing amounts of THC adsorbed to albumin in solutions comprising varying concentrations of THC at two different times of incubation.

An albumin solution in water (20 μg/ml) and ethanol was prepared. THC standard was added at concentrations of between 20 μg/ml and 60 μg/ml. The amount of THC adsorbed to the BSA protein was determined for each concentration after incubation for either two hours or 12 hours while gently vortexing. The results are shown in FIG. 4. As seen in the figure, concentrations of above 0.5 μg adsorbed THC per mg of albumin can be obtained. It is suggested that compositions according to embodiments of the invention comprising mixtures of cannabinoids can be adsorbed to proteins in similar concentration ranges.

Example 1f: Formation of Protein-Bound Cannabinoid from Cannabis Vapor Using Additional Proteins Vapor of cannabis plant material high in CBD was formed using a volcano vaporizer, and the vapor was streamed through 1 mg/ml solutions of either rice recombinant human serum albumin (HSA), bovine γ-globulin or ovalbumin (hen). The protein solutions were formed using ethanol and water in a 1:2 ratio. The solutions were incubated at 30° C. for 24 hours. The percentage of each cannabinoid relative to total cannabinoids adsorbed to protein was determined and is shown in the table below.

| Cannabinoid | Rice recombinant HSA | Bovine γ-globulin | Ovalbumin |
|---|---|---|---|
| CBDA | 46 | 0 | 2.4 |
| CBGA | 0 | 0 | 0 |
| CBG | 0 | 0 | 0 |
| CBD | 33 | 0 | 55.9 |
| CBN | 0 | 0 | 0 |
| THCA | 0 | 100 | 0 |
| THC | 21 | 0 | 41.7 |
| CBC | 0 | 0 | |

These results indicated that HSA and ovalbumin act similarly to BSA. The HSA and the ovalbumin each adsorbed about 4 micrograms of cannabinoid per mg of protein. On the other hand, γ-globulin adsorbed lower levels of cannabanoid and a different profile.

Example 2a: Formation of Protein-Bound Cannabinoid from Cannabis Extract

Cannabis extract was prepared as follows: In short, cannabis plant matter is dried, ground and homogenized to form ground cannabis. The ground cannabis is extracted with methanol/chloroform (volume/volume ratio of 9:1). Sonication and filtration is then performed. Identity of cannabinoids is determined by HPLC by evaporation, dissolution in an appropriate solvent.

Drying of the cannabis plant matter occurs under high vacuum at about 37±2° C. for about 24 hours and then ground to form a fine powder. 200 mg of ground powder is combined with 10 ml of methanol/chloroform, and sonicated in an ice bath for 30 minutes at maximum power. The supernatant is then filtered through a 0.2 micron filter.

A sample of the cannabis extract was analyzed for content of cannabinoids. The cannabis extract was then combined with albumin solution having 20% ethanol at 10 mg/ml (BSA) and incubated for 2 hours at room temperature. The percentage of each cannabinoid relative to total cannabinoids adsorbed to protein was determined and is shown in the table below.

| Cannabinoid | Extract | Adsorbed to BSA after extract combined with BSA solution |
|---|---|---|
| CBDA | 1 | 0 |
| CBGA | 3 | 2 |
| CBG | 3 | 1 |
| CBD | 0 | 0 |
| CBN | 2 | 2 |
| THCA | 22 | 29 |
| THC | 68 | 63 |
| CBC | 1 | 3 |

This experiment shows a different profile than the profile of cannabinoids in experiment 1 in which cannabinoids from vapor were adsorbed in protein solutions. The weight ratio of adsorbed cannabinoids to protein in this experiment was about 1 to 5.

Example 2b: Formation of Protein-Bound Cannabinoid from Cannabinoid Solution Cannabis buds, (3 g) from a high THC strain, obtained from Seach Ltd, Israel was rolled into cigarettes and was burnt or vaporized and the resulting smoke and vapor was combined with 200 ml ethanol. The 200 ml solutions were concentrated to a volume of about 3 ml. The amount of cannabinoids dissolved in ethanol from smoke and vapor was determined and is described (in micrograms/ml) in the table below:

|  | Vapor | Smoke |
|---|---|---|
| CBDA | 3.1218 | 0 |
| CBGA | 28.7668 | 23.088 |
| CBG | 183.6224 | 292.063 |
| CBD | 17.2726 | 0 |
| CBN | 135.5254 | 276.856 |
| THCA | 72.8432 | 83.765 |
| THC | 3777.7796 | 6195.223 |
| CBC | 54.7468 | 90.873 |
| delta-8-THC | 0 | 0 |
| Total Cannabinoids | 4273.6786 | 6961.868 |

100 microliters of ethanolic cannabinoid solution from cannabis vapor and cannabis smoke were each mixed with 500 microliters of aqueous albumin solution that had been prepared at a concentration of 5 mg albumin (BSA)/ml. The aqueous albumin solution combined with the ethanolic cannabinoid solution was incubated at 30° C. for 12 hours in open tubes. After 12 hours, the tubes were mixed and centrifuged, and non-adsorbed cannabinoids were separated from the solution. Concentrated protein-bound cannbinoid was dried and quantified as described below.

|  | Vapor | Smoke |
|---|---|---|
| CBDA | 0 | 0 |
| CBGA | 1.43 | 0.58 |
| CBG | 11.685 | 5.9 |
| CBD | 0 | 0 |
| CBN | 4.855 | 6.5 |
| THCA | 4.26 | 2.16 |
| THC | 131.955 | 121.38 |
| CBC | 1.845 | 2.13 |
| delta-8-THC | 4.6 | 0 |
| Total Cannabinoids | 160.63 | 138.645 |

Example 3: Formation of Protein-Bound Opioid from Opium

Protein bound-opium may be formed using similar methods described with reference to protein-bound cannabinoids.

Example 4a: Biological Effect of Protein-Bound Cannabinoid Relative to Non-Bound Cannabinoid The NFκB transcription factor plays a key role in inflammation, the immune response, cell proliferation and protection against apoptosis.

The murine macrophage cell line RAW264.7 (obtained from the American Type Culture Collection) was transduced with an NF-κB luciferase reporter construct and used in the assay to determine inhibitory effects of test compositions on NF-κB protein in cells containing the NF-κB luciferase reporter gene construct. The test compositions used were raw plant extract from cannabis high in THC and protein-bound cannabinoid mixture prepared from cannabis plant extract derived from the same cannabis plant material, prepared as described above. Inhibition was determined at two doses, 1.56 micrograms per milliliter (μg/ml) and 0.78 μg/ml of THCA. Plant extract was dissolved in medium before adding to cell culture. Lipopolysaccharide (LPS) was used to induce NF-κB luciferase reporter and the extracts were tested for inhibitory activity. Calcein AM (acetomethoxy derivate of calcein) was used as a fluorescent dye to determine RAW264.7 cell number for normalization. As luminescence in the model is correlated to activation of NF-κB, inhibition of expression can be determined by correlation with inhibition of luminescence.

Figure 3A:
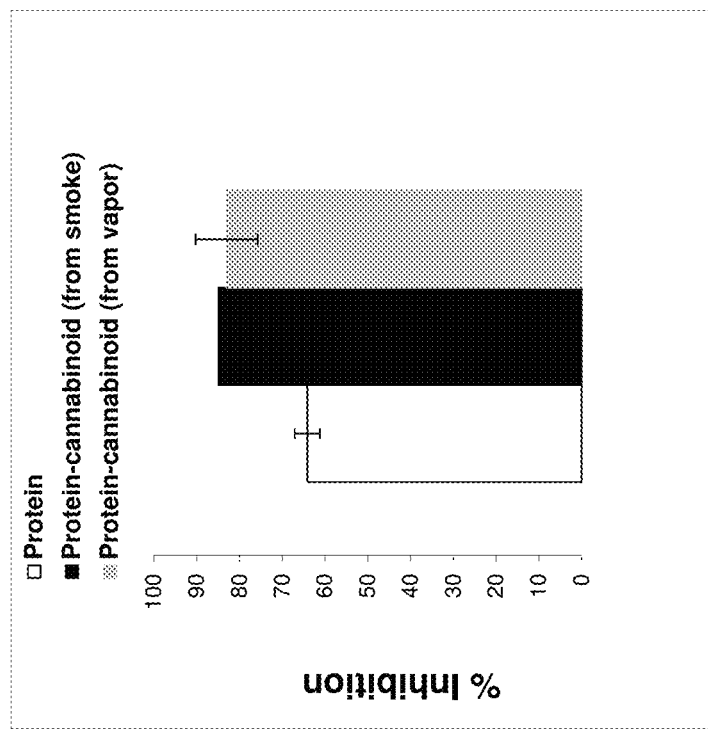
FIG. 3A depicts a graph showing inhibition of nuclear factor-kappaB (NFκB), an indicator of inflammation, at two concentrations for two cannabinoid compositions obtained by known methods, versus cannabinoid compositions obtained according to embodiments of the invention.

Compositions with high percentage of inhibition in the model indicate their potential use to reduce inflammation by inhibition of NF-κB activity in mammals. The effects of both plant extract and protein-bound cannabinoid on NF-κB luciferase reporter at concentrations of 1.56 and 0.78 μg/ml of THCA were tested and are shown in FIG. 3a. At both concentrations, protein-bound cannabinoid was more effective in inhibition NF-κB luciferase reporter induction than raw cannabis plant extract, indicating that protein-bound cannabinoid has enhanced anti-inflammatory properties relative to raw cannabis plant extract and is effective at lower doses.

In subsequent experiments, protein-bound cannabinoid was extensively washed using Amicon Ultra Centrifugal Filters having a cutoff of 30 kilodaltons. Samples were washed with 0.5 ml of water and repeated 1, 2 or 4 times. Samples washed 1, 2 and even 4 times showed similar effect on inhibition in the model, indicating that the cannabinoids were strongly adsorbed by the albumin, however they maintained their bioactive properties when exposed to cells.

Example 4b: Biological Effect of Protein-Bound Cannabinoid Relative to Non-Bound Cannabinoid The in-vitro model described in example 4a was performed, comparing protein-bound cannabinoid prepared from smoke and protein-bound cannabinoid prepared from vapor at a concentration of 6 micrograms/ml, prepared as described in example 2b. Protein alone, in an equivalent amount, was used as a control.

Figure 3B:
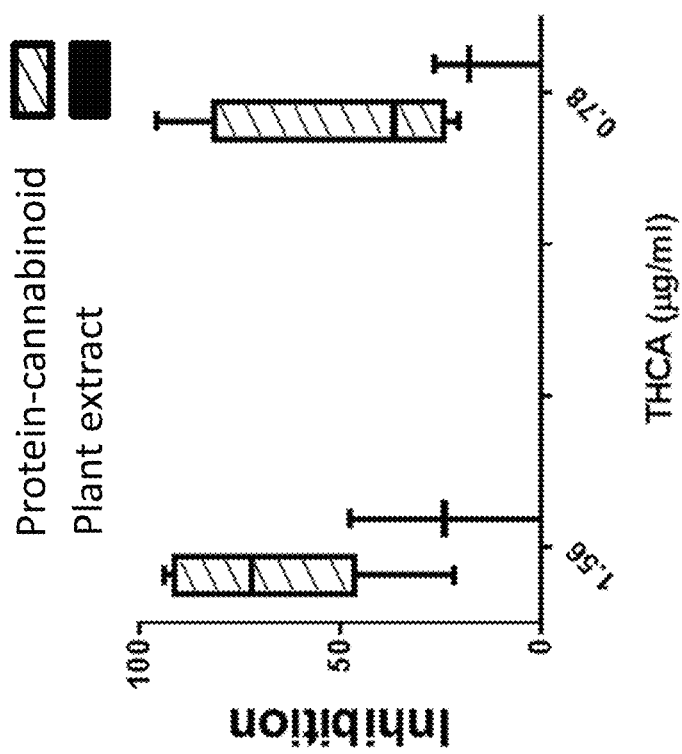
FIG. 3B depicts a graph showing inhibition of nuclear factor-kappaB (NFκB), using cannabinoid compositions obtained according to embodiments of the invention.

The effects of protein alone and protein-bound cannabinoid are shown in FIG. 3b. Both protein-bound cannabinoid obtained from smoke and obtained from vapor were more effective in inhibition NF-κB luciferase reporter induction than protein alone.

Example 5a: In Vivo Testing of Cannabinoids According to Embodiments of the Invention in a Model of Appetite Increase Mice (C57BL strain) are isolated from each other and fed at regular intervals for one week. Mice are grouped into groups of 4. After the week of regular feeding, food is removed from each mouse's cage for 24 hours. Thirty minutes before providing food, each mouse is administered a test drug, positive control (ethanolic cannabis extract or pure THC) or a negative control comprising vehicle only. A measured amount of food is provided after the 24 hours without food. One hour and two hours after provision of the food, the remaining amount of food is weighed and compared to the starting amount of food. Test mice are administered with one of the doses (1, 2, 3 or 6 mg of THC equivalent/kg of mouse weight) of protein-bound cannabinoid, in a phosphate buffered saline (PBS) in an amount of 100 microliters through either the intraperitoneal (IP), nasal or oral (gavage) routes. Positive control mice are administered 1, 2, 3 or 6 mg of THC (or equivalent) in the form of ethanolic extract of cannabis dissolved in PBS, or pure THC dissolved in ethanol, dissolved in PBS in 100 microliters through either the intraperitoneal (IP), nasal or oral (gavage) routes. Negative control mice are administered ethanol in PBS through either the intraperitoneal (IP), nasal or oral (gavage) routes. Trials are repeated in triplicate and the results are tallied by blinded researchers.

It may be shown that mice administered doses of protein-bound cannabinoid are effective in increasing appetite in mice relative to mice receiving no active treatment. It is suggested that mice administered doses of protein-bound cannabinoid may experience appetite increase to a greater extent than the mice administered equivalent doses of non-protein bound cannabinoid.

Example 5b: In Vivo Testing of Cannabinoids According to Embodiments of the Invention in a Model of Neuropathy and Neuropathic Pain Mice (C57BL strain) are grouped into groups of 8. Each mouse is administered Vincristine throught the IP route, twice a week for 10 weeks, at an amount of 1.7 mg/kg. Mice are administered test drug, positive control or negative control. The mice are tested once a week for sensitivity to pain using a hot plate, rotarod test and a tail flick test, for 10 weeks. Test mice are administered with one of the doses (1, 2, 3 or 6 mg of THC equivalent/kg of mouse weight) of protein-bound cannabinoid, in a phosphate buffered saline (PBS) in an amount of 100 microliters through the nasal route. Positive control mice are administered 1, 2, 3 or 6 mg of THC (or equivalent) in the form of ethanolic extract of cannabis dissolved in PBS, or pure THC dissolved in ethanol, dissolved in PBS in 100 microliters through the nasal route. Negative control mice are administered ethanol in PBS through the nasal route. Trials are repeated in triplicate and the results are tallied by blinded researchers.

It may be shown that mice administered protein-bound cannabinoid withstand pain for longer, and thereby show longer time until tailflick or leglift upon hotplate testing, and show more success in rotarod testing.

Example 5c: In Vivo Testing of Cannabinoids According to Embodiments of the Invention in a Model of Parkinson's Disease Mice (C57BL strain) are grouped into groups of 8. Each mouse is administered two doses, of 20 mg/kg of 1-methyl-4-phenyl-1,2,3,6-tetrahydropyridine (MPTP) with an hour wait between the administrations. After 48 hours, each mice is administered another two doses an hour apart from each other.

Mice are administered test drug and control as described in example 5b. Mice are tested for Parkinsonian symptoms using footprint analysis, a rotarod test, a hot plate and a tailflick test.

It may be shown that mice administered protein-bound cannabinoid show an improvement in Parkinsonian symptoms induced by MPTP relative to mice from control groups.

There is further provided in accordance with an embodiment of the invention, a composition comprising at least one pharmaceutically acceptable excipient and at least one protein-bound cannabinoid bound to a plasma protein. Optionally, the composition further comprises water. Optionally, the composition is substantially free of water. Optionally, the plasma protein comprises one of or a combination of more than one of albumin, lipoprotein, glycoprotein, $\alpha$, $\beta$, and $\gamma$ globulin and diluted blood plasma. Optionally, the protein comprises albumin. Optionally, the albumin comprises human serum albumin, bovine serum albumin or egg albumin (OVA). Optionally, plasma protein is a recombinant protein. Optionally, the composition comprises less than 10% non-protein-bound cannabinoid. Optionally, the ratio of protein to cannabinoid is between 100:1 to 1:1 according to a weight/weight basis Optionally, the ratio of protein to cannabinoid is between 20:1 to 1:1 according to a weight/weight basis. Optionally, the cannabinoid is selected from the group consisting of: $\Delta$9-THC, $\Delta$8-THC, tetrahydrocannabinoic acid (THCA), CBD, cannabidiolic acid (CBDA), cannabinol (CBN), cannabigerol (CBG), tetrahydrocannabivarin (THCV), cannabigerolic acid CBGA and cannabichromene (CBC). Optionally, the composition further comprises an additional active pharmaceutical agent. Optionally, the composition comprises a targeting moiety linked to the plasma protein.

There is further provided in accordance with an embodiment of the invention, a method for the manufacture of a protein-bound cannabinoid, the method comprising: obtaining a cannabinoid or cannabis in a form selected from the group consisting of cannabis smoke, cannabis vapor, cannabinoid solution and cannabis extract; and combining the cannabinoid or cannabis with an aqueous solution or suspension comprising a plasma protein to form a protein-bound cannabinoid. Optionally, the method comprises, obtaining cannabis in a form selected from the group consisting of cannabis smoke, cannabis vapor and cannabis extract, and combining the cannabis smoke, vapor or extract with an aqueous solution or suspension comprising a plasma protein to form a protein-bound cannabinoid. Optionally, the method comprises, heating cannabis plant matter to form the cannabis smoke or the cannabis vapor, and contacting the smoke or vapor with the aqueous solution or suspension comprising a plasma protein. Optionally, the method comprises, heating cannabis plant matter to form cannabis smoke or cannabis vapor, contacting the smoke or vapor with a solvent to form the cannabinoid solution; and combining the cannabinoid solution with the aqueous protein solution or suspension comprising a plasma protein. Optionally, the solvent is an alcohol. Optionally, the alcohol is ethanol. Optionally, the method comprises, isolating the protein-bound cannabinoid from solution. Optionally, the cannabinoid is burnt to form the smoke. Optionally, the method comprises, forming the cannabis extract by combining cannabis plant matter with a solvent. Optionally, the solvent comprises an alcohol. Optionally, the solvent comprises methanol and chloroform. Optionally, the method comprises, removing non-protein-bound cannabinoids. Optionally, the plasma protein comprises one of or a combination of more than one of albumin, lipoprotein, glycoprotein, α, β, and γ globulin and diluted blood plasma. Optionally, the protein comprises albumin. Optionally, the albumin comprises human serum albumin, bovine serum albumin or egg albumin (OVA). Optionally, the method comprises, after removing non-protein-bound cannabinoids, the resulting composition comprises less than 10% by weight non-protein-bound cannabinoid. Optionally, the protein-bound cannabinoid comprises one or more than one of the cannabinoids selected from the group consisting of: Δ9-THC, Δ8-THC, tetrahydrocannabinoic acid (THCA), CBD, cannabidiolic acid (CBDA), cannabinol (CBN), cannabigerol (CBG), tetrahydrocannabivarin (THCV), cannabigerolic acid CBGA and cannabichromene (CBC). Optionally, the aqueous solution or suspension further comprises an alcohol. Optionally, the alcohol is present in a range of between 1% to about 33% of the solution. Optionally, the ratio of plasma protein to cannabinoid upon combining is between 2:3 and 1:10. Optionally, the method comprises stirring the aqueous solution or suspension. Optionally, the aqueous solution or suspension is stirred for about 24 to about 48 hours. Optionally, the aqueous solution or suspension is at a temperature of about 30° C. Optionally, the aqueous solution or suspension is under vacuum.

There is further provided in accordance with an embodiment of the invention, a method for treating a disease comprising administering to a patient in need thereof a composition comprising at least one pharmaceutically acceptable excipient and at least one protein-bound cannabinoid bound to a plasma protein. Optionally, the disease is selected from the group consisting of: conditions of pain relating to chemotherapy; conditions of pain and "wasting" syndrome in connection with AIDS; nausea and vomiting, nausea and vomiting as side effects of a chemotherapy as well as in connection with AIDS or hepatitis; neuropathic pain; anorexia or cachexia; neurodegenerative disease; hypoxia, comprising stroke or trauma; paralytic symptoms in connection with multiple sclerosis or traumatic transverse lesions; dystonic motor disturbance; bronchial asthma; epileptic attacks or generalized epilepsy; withdrawal symptoms in connection with alcohol dependence, benzodiazepine dependence and opiate dependence; Parkinson's disease; dementia, Alzheimer's disease; arthritis; glaucoma; migraine; PTSD; Crohn's disease; tremor, Parkinsonian tremor; attention deficit disorder; attention deficit hyperactivity disorder; irritable bowel syndrome and dysmenorrhoea.

There is further provided in accordance with an embodiment of the invention, a unit dose pharmaceutical composition comprising a composition comprising at least one pharmaceutically acceptable excipient and at least one protein-bound cannabinoid bound to a plasma protein. Optionally, the unit dose pharmaceutical composition comprises an amount between 1 mg and 1 g. Optionally, the unit dose pharmaceutical composition is in the form of a tablet, capsule, lozenge, wafer, patch, ampoule, vial, metered-dose inhaler or pre-filled syringe.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

WORKS CITED

Casano, S et al. "Variations in Terpene Proviles of Different Strains of *Cannabis sativa* L. Aca Hort. 925, ISHS 2011.
De Backer, B., 2009. Innovative development and validation of an HPLC/DAD method for the qualitative and quantitative determination of major cannabinoids in cannabis plant material. *J. Chromatogr.*, Volume B 877, pp. 4115-4124.
ElSohly, M. A. ed. Forensic Science and Medicine: Marijuana and the Cannabinoids. Chapter II, pages 17-49
Greydanus, D., 2013. Marijuana: current concepts. *Frontiers in Public Health*, Volume 1, pp. 1-17.
Melamede, R., 2005. Cannabis and tobacco smoke are not equally carcinogenic. *Harm Reduction Journal*, 2(21).
Naftali, T., 2011. Treatment of Crohn's Disease with Cannabis: *IMAJ*, Volume 13, pp. 455-8.
Pletcher, M., 2012. Association Between Marijuana Exposure. *Journal of American Medical Association*, 307(2), pp. 173-181.

The invention claimed is:

1. A tablet or capsule consisting essentially of a cannabis extract consisting essentially of at least one phyto-cannabinoid bound to a protein, wherein the protein is selected from the group consisting of: albumin, α globulin, β globulin, and γ globulin.

2. The tablet or capsule according to claim 1, wherein the protein is albumin.

3. The tablet or capsule according to claim 1, wherein the albumin is selected from the group consisting of recombinant albumin, human serum albumin, bovine serum albumin and egg albumin.

4. The tablet or capsule according to claim 1, wherein the phyto-cannabinoid is selected from the group consisting of Δ9-tetrahydrocannabinol, Δ8-tetrahydrocannabinol, tetrahydrocannabinoic acid, cannabidiol, cannabidiolic acid, cannabinol, cannabigerol, tetrahydrocannabivarin, cannabigerolic acid, and cannabichromene.

5. The tablet or capsule according to claim 4, wherein the phyto-cannabinoid is cannabidiol.

6. The tablet or capsule according to claim 1, wherein the phyto-cannabinoid is bound to one or more hydrophobic regions of the protein.

7. The tablet or capsule according to claim 1, wherein the amount of phyto-cannabinoid in the tablet or capsule is between 1 mg and 1 g.

8. The tablet or capsule according to claim 1, wherein the amount of protein-bound phyto-cannabinoid is between 0.1% and 95% of the tablet or capsule.

9. The tablet or capsule according to claim 1, wherein the amount of protein-bound phyto-cannabinoid is between 1% and 70% of the tablet or capsule.

* * * * *